(12) United States Patent
Berke

(10) Patent No.: US 10,286,230 B2
(45) Date of Patent: May 14, 2019

(54) GAUGE FOR DOSE MEASUREMENT IN RADIATION THERAPY AND METHODS FOR VERIFYING A RADIATION THERAPY DEVICE

(71) Applicant: KUKA Deutschland GmbH, Augsburg (DE)

(72) Inventor: Ralph Berke, Gessertshausen (DE)

(73) Assignee: KUKA Deutschland GmbH, Augsburg (DE)

( * ) Notice: Subject to any disclaimer, the term of this patent is extended or adjusted under 35 U.S.C. 154(b) by 597 days.

(21) Appl. No.: 13/945,338

(22) Filed: Jul. 18, 2013

(65) Prior Publication Data

US 2014/0054465 A1 Feb. 27, 2014

(30) Foreign Application Priority Data

Aug. 21, 2012 (DE) .................. 10 2012 214 820

(51) Int. Cl.
*A61N 5/10* (2006.01)
*G01T 1/169* (2006.01)

(52) U.S. Cl.
CPC ............ *A61N 5/1075* (2013.01); *G01T 1/169* (2013.01); *A61N 2005/1076* (2013.01)

(58) Field of Classification Search
CPC .................. A61N 5/10; A61N 5/1075; A61N 2005/1076; G01T 1/169
USPC ...................................................... 250/358.1
See application file for complete search history.

(56) References Cited

U.S. PATENT DOCUMENTS

| | | | |
|---|---|---|---|
| 7,420,160 B2 | 9/2008 | Delaperriere et al. | |
| 7,902,515 B2 | 3/2011 | Navarro | |
| 2005/0228255 A1* | 10/2005 | Saracen | A61B 6/0457 600/407 |
| 2006/0002511 A1* | 1/2006 | Miller | A61N 5/107 378/65 |
| 2007/0140413 A1* | 6/2007 | Saracen | A61B 6/08 378/18 |

(Continued)

FOREIGN PATENT DOCUMENTS

| | | |
|---|---|---|
| DE | 102010047356 A1 | 4/2012 |
| DE | 10 2010 061 121 A1 | 6/2012 |

(Continued)

OTHER PUBLICATIONS

German Patent Office; Search Report in German Patent Application No. 10 2012 214 820.5 Published Dec. 18, 2012; 6 pages.

(Continued)

*Primary Examiner* — David P Porta
*Assistant Examiner* — Gisselle M Gutierrez
(74) *Attorney, Agent, or Firm* — Dorton & Willis, LLP

(57) ABSTRACT

A measuring device for measuring a radiation dose, and a method for checking a radiotherapy device is disclosed. The measuring device includes a water phantom, a mechanical device designed to move the water phantom, and a control device. The water phantom includes a detector device which is adapted to detect ionizing radiation, and the control device is designed to control the mechanical device in such a manner that it moves the water phantom according to a movement of a patient, which the patient makes during an irradiation with a radiotherapy device.

15 Claims, 2 Drawing Sheets

(56) References Cited

U.S. PATENT DOCUMENTS

2009/0168961 A1* 7/2009 Hieronimi et al. ............. 378/65
2010/0176284 A1* 7/2010 Navarro ..................... 250/252.1

FOREIGN PATENT DOCUMENTS

GB           2471750 A    1/2011
WO      2006113323 A2   10/2006

OTHER PUBLICATIONS

Nioutsikou et al.; Publication Entitled "Dosimetric Investigation of Lung Tumor Motion Compensation With a Robotic Respiratory Tracking System: An Experimental Study" Published Apr. 2008; 10 pages.
Naisbit et al.; Publication Entitled "Towards Automatic Quality Assurance of KV-MV Isocentre Coincidence" Published Jun. 2011; 1 page.
PTW-Freiburg; Publication Entitled "Proton Therapy QA Tools" Published 2007; 4 pages.
Jani et al.; Publication Entitled "Utility of Maximum Intensity Projection of Gated PET Images in Determining Target Volumes of Moving Lung Tumors: A Phantom Study" Published Jun. 2011; 1 page.
European Patent Office; Search Report in European Patent Application No. 13178499.3 dated Nov. 7, 2017; 16 pages.
D'Souza et al.; Publication entitled "Real-Time Intra-Fraction-Motion Tracking Using the Treatment Couch: A Feasibility Study" published Aug. 11, 2005; 13 pages.

* cited by examiner

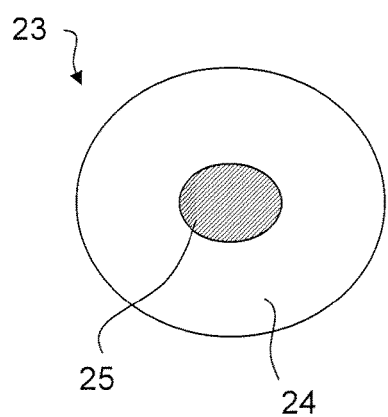
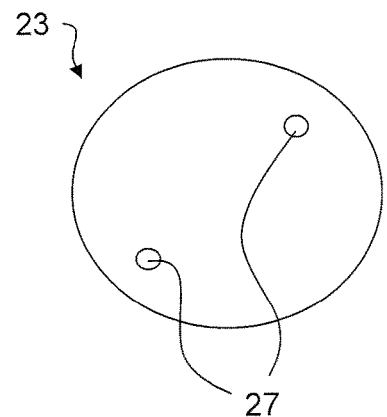
FIG. 3                FIG. 4
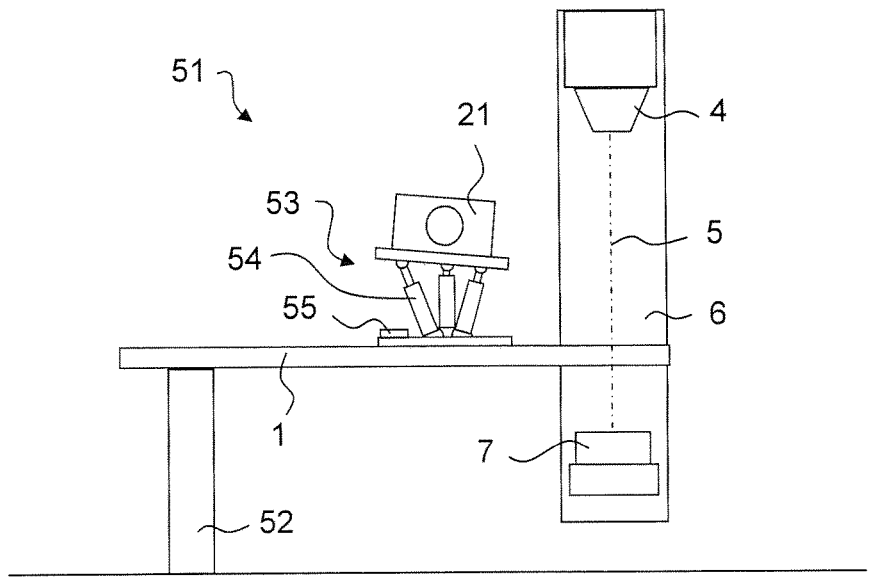
FIG. 5

GAUGE FOR DOSE MEASUREMENT IN RADIATION THERAPY AND METHODS FOR VERIFYING A RADIATION THERAPY DEVICE

TECHNICAL FIELD

The invention relates to a measuring device for measuring the radiation dose, and the method for checking a radiotherapy device.

BACKGROUND

Radiotherapy devices are for example known from GB 2471750 A. These typically include a treatment table, a support device, for example in the form of a rotating gantry, and a therapeutic radiation source fixed to the support device. During the specified normal operation of the radiotherapy device, the therapeutic radiation source generates ionizing radiation, such as used for the X-radiation or gamma radiation, or high-energy electrons, protons or ion beams.

For example, to check the radiotherapy device or to schedule an exposure of a patient by means of the radiotherapy device, water phantoms can be used that are known for example from U.S. Pat. No. 7,420,160 B2.

SUMMARY

The technical task of the invention is to provide an improved measurement device for measuring the dose in radiotherapy.

Another task of the invention is to provide an improved procedure to check a radiotherapy device.

The task of the invention is achieved by a measuring device for dose measurements in radiotherapy, which comprises
  a water phantom with a detector device, which is formed so as to detect an ionizing radiation,
  a mechanical device that is formed so as to move the water phantom, and
  a control device that is formed so as to control the mechanical device such that the water phantom moves according to a movement of the patient that the patient makes during an irradiation with a radiotherapy device.

The further technical task of the invention is achieved by a method for checking a radiotherapy device comprising the steps of:
  placing a water phantom on a treatment table of a radiotherapy device, which includes a robot arm, a control device, and a radiation source, wherein the robot arm comprises a plurality of elements following in succession that are connected by joints and are movable relative to each other with respect to their axes, the treatment table is fixed to the robot arm, the control device is so formed as to move the robot arm, and the water phantom comprises a detector device formed as to detect an ionizing radiation, and
  irradiating of the water phantom placed on the treatment table by the radiation source and, controlled by the control device, simultaneously moving the robot arm so that the water phantom performs a movement in accordance with the movement of the patient.

The further technical task of the invention is also achieved by a method for checking a radiotherapy device, comprising the steps of:
  placing a water phantom and a mechanical device on a treatment table of a radiotherapy device, wherein the mechanical device is formed as to move the water phantom,
  irradiation of the water phantoms placed on the treatment table using a radiation source of the radiotherapy device and simultaneously moving the mechanical device, so that the water phantom performs a movement according to a movement of a patient.

The measuring device according to the invention accordingly comprises the water phantom and the mechanical device. Water phantoms as such are known to a person skilled in the art, and are provided to measure the dose of the radiation generated by the radiotherapy device during its testing. The water phantom comprises, for example, a container filled with a liquid, in which the detector device is arranged.

The mechanical device is provided to move the water phantom during the irradiation. The mechanical device can be formed, for example, as a robotic arm that comprises consecutively following elements, which are connected by joints and are movable relative to each other with respect to their axes. The robot arm can be in particular part of the radiotherapy device to be tested and also be provided to hold a treatment table for a patient to be irradiated. Thus, it can be placed on the treatment table for the irradiation of the water phantom.

The mechanical device can also be designed as a mechanical component of a hexapod. Hexapods can be designed relatively small, making it possible for the water phantom to be placed with the hexapod on the patient couch of the radiotherapy device for irradiation.

According to the invention, the mechanical device, in particular the robot arm or the hexapod, is designed so that the water phantom performs a movement corresponding to a movement that the patient performs during its irradiation. The movement of the patient is caused, for example, by respiration of the patient. This allows to better simulate the irradiation of the patient by means of the water phantom. Based on the result of this simulation, or based on the evaluation of the detector device of the water phantom after, the treatment table can be better moved for the irradiation of the patient, in order to at least partially compensate the movement of the patient during the irradiation. Thus, it may in particular be provided to move the treatment table by means of the robot arm during an irradiation of the patient based on the evaluated detector device.

The detector device may preferably comprise a main body and at least one detecting means, which is arranged or can be arranged in or on the main body. The main body may preferably be made of a material that absorbs the radiation generated by the radiation source of the radiotherapy device, at least approximately, as much the body of the patient to be irradiated. The radiotherapy device is in particular intended to irradiate a tumor of the patient. The radiation absorption ability of the material of the main body can then in particular correspond at least approximately to that of the tumor. A suitable material is for example cork.

Preferably, the main body may comprise an inner body and an outer body, which encloses the inner body. The size of the inner body can, for example, at least approximately correspond to the size of the tumor to be irradiated. The radiation absorption ability of the material of the inner body can then in particular correspond at least approximately to that of the tumor. The radiation absorption ability of the material of the outer body can then in particular correspond at least approximately to that of the tissue surrounding the tumor.

The at least one detector means can comprise, for example, an X-ray film. In this case, it can be preferably provided that the main body comprises least comprises a slot, in which the X-ray film can be slid. Preferably, the main body comprises several slots, into each of them an X-ray film can be inserted. Then it is possible to obtain a three-dimensional radiation dose distribution after the irradiation of the water phantom.

The at least one detector means may additionally or alternatively comprise at least one radiation detector arranged in and/or on the main body. This detector creates, for example during the irradiation, electric signals, which are associated with the radiation dose. These can be then for example automatically evaluated.

For example, for the X-ray-free detection of the tumor position of the patient, for example, breathing models or implantable probes with external detection could be used, for example, on the skin surface. In particular by means of the methods of the invention that may relate to a robotic measurement phantom, individual situations of the patient can be simulated. This robot-guided phantom preferably images a physical human model that simulates the potential tumor shift in the target area and allows a 3-D measurement of the radiation dose distribution in the interior space of the model.

If appropriate, a robot or hexapod, etc. guides the measurement model (water phantom). The phantom is in particular designed so that, for example X-ray films can be placed between a disc-like phantom design. In addition, various tissue structures can be simulated in the model, where appropriate, for example, by incorporating cork or similar materials. This allows to recreate a realistic physiological model for 3-D dosimetry of the simulated tumor and the tumor environment.

If necessary, the data from the pre-recorded simulated phantom can be combined with the (on-line) measured patient sensor measurement data in order to calculate the potential tumor movement. During irradiation, using an appropriate control algorithm (mathematical models), one can predict the location of the tumor, for example, to save computation time. Also, a suitable compensation vector can be derived and the current tumor deflection can be compensated by a counter-movement of the robot. Thus, one can ensure that a constant tumor location can be achieved and thus a constant dose distribution can be effected during the irradiation of the patient.

BRIEF DESCRIPTION OF THE DRAWINGS

Embodiments of the invention are illustrated in the appended schematic drawings. The figures show:

FIGS. 3, 4 show the detector device in a cross-section, and FIG. 5 shows a further radiotherapy device.

DETAILED DESCRIPTION

Figure 1:
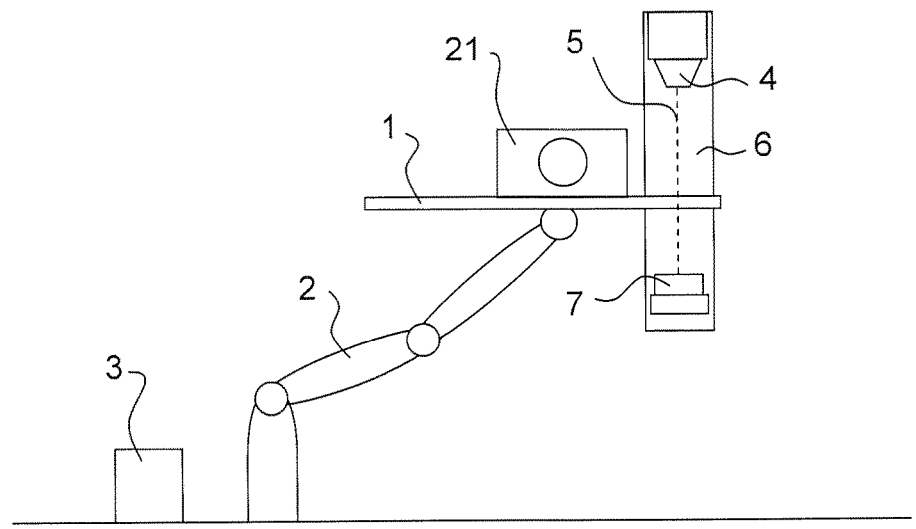
FIG. 1 shows a radiotherapy device.

FIG. 1 shows a radiotherapy device. In the exemplary embodiment, it comprises a treatment table 1 and a robot arm 2, which has a plurality of successively following elements, which are connected by joints and are movable relative to each other with respect to their axes. At one end of the robot arm 2 is attached the treatment table 1. In the case of the present embodiment, the patient support 1 is provided so that a patient (not shown) can lie on it.

The robot arm 2 comprises drives, in particular electrical drives, which are connected to a control device 3 of the radiotherapy device. The electric drives are preferably controlled electric drives. By means of the drives, the robotic arm 2 or its elements are moved relative to each other and controlled by the control device 3, or by a computer program running on the control device 3.

The radiotherapy device also comprises a therapeutic radiation source 4, which is controlled for example by means of the control device 3. During a proper operation of the radiotherapy device, the therapeutic radiation source 4 generates an ionizing radiation, such as X-ray or gamma radiation, or high-energy electron, proton or ion radiation used for radiotherapy, whose central ray is shown in FIG. 1 in dashed lines. The radiotherapy device further comprises a support means 6, to which is attached the therapeutic radiation source 4. The support device 6 is designed, for example as a rotatable gantry, as is known in principle to a person skilled in the art.

The radiotherapy device may comprise an optical receiver 7, which is also attached to the support device 6, and on which the ionizing radiation is incident. By means of the radiation receiver 7, one can produce, for example, portal images.

The radiotherapy device is provided to irradiate a tumor of the patient. In the control device 3, for example, is running a computer program, by means of which the control device 3 so controls the robot arm 2 that during the irradiation, it at least partially compensates for a movement of the patient.

Figure 2:
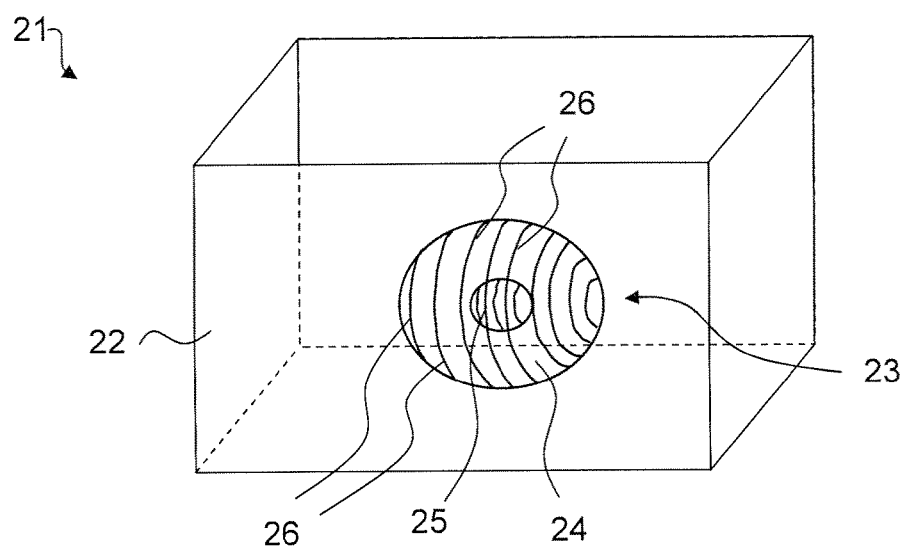
FIG. 2 shows a water phantom that comprises a container filled with a fluid and a detector device arranged within the container.

The water phantom 21, shown in FIG. 2 is a perspective view, is used in the case of the present embodiment, for example, to carry out a dose measurement for radiation therapy and/or to obtain data of the patient prior to irradiation, which allow improved prediction of the movement of the patient during the irradiation, in order to, for example, better move the treatment table 1 by the robot arm 2 for at least a partial compensation of the patient's movement.

The water phantom 21 is provided to measure ionizing radiation, such as the ionizing radiation generated by the therapeutic radiation source 4 in terms of its radiation parameters and its effect on the human body.

In the case of the present embodiment, the water phantom 21 comprises, for example, a rectangular container 22, which is open upwards and can be filled with a liquid, in particular water. The water phantom 21 further comprises a detector means 23, which is designed so as to measure the ionizing radiation entering the liquid. The detector device 23 is secured, for example, by a non-illustrated holding device to container 22. FIGS. 3 and 4 show the detector device 23 in a cross-section.

In the case of the present embodiment, the detector device 23 comprises in particular a spherically shaped outer body 24, which encloses an inner main body 25. The outer body 24 is in particular made of a material that is associated with the part of the body of the patient to be irradiated with the radiotherapy device. This material absorbs in particular the ionizing radiation according to the tissue of the body part. The outer body 24 is made for example of cork. The inner main body 24 is made in particular of a material that corresponds to a tumor of this body part.

In the case of the present embodiment, the detector device 23 comprises at least one detector means, by which the ionizing radiation can be measured. The said detecting means is, for example, at least one X-ray film 26, which is or can be inserted into a slot or into the slots of the two main bodies 24, 25. For this purpose, the two main bodies 24, 25 are designed, for example, like a disk.

Additionally or alternatively, at least one radiation detector can be designed as a detector means 27, which is disposed in the outer body 24 and/or inner body 25.

In the case of the present embodiment, the water phantom 21 is used in combination with the robot arm 2 as a measuring device for measurement of the radiation dose. The water phantom 21 is placed on the treatment table 1 and the robot arm 2 is automatically moved by the control device 3 such that a movement of the patient is simulated during the irradiation. The movement of the patient during the irradiation is caused, for example, by respiration of the patient. In order to suitable move the robot arm 2, a suitable computer program is running in particular in the control device 3, so that the control device 3 actuates the drives of the robot arm 2 for the treatment table 1 and thus also the water phantom 21 to perform the simulated movement. To simulate the movement of the patient, for example, a mathematical model of the movement of the patient is loaded in the control device 3.

While the robot 2 is controlled such that the water phantom 21 carries out the simulated movement, the water phantom 21 is irradiated with the therapeutic radiation source 4. Due to this irradiation, the water phantom 21 and in particular the detection device 23 are exposed to a radiation dose that can be analyzed after the irradiation by the detectors means, for example the at least one X-ray film 26 and/or the at least one radiation detector 27.

Thus it is possible, by means of the robot arm 2, which is generally a mechanical device for moving the water phantom 21, to preferably simulate individual patient situations as realistically as possible. The robot arm 2, controlled by the control device 3, guides the water phantom 21 during irradiation of the phantom, and simulates the anticipated movement of the tumor or the tumor displacement of the patient. The movement of the tumor is shown on the water phantom 21. The particularly round detector device 23 of the water phantom 21 is in particular designed so that, for example, X-ray films 26 can be introduced between the, for example, disk-like ball design of the detector device 23. In addition, in the ball model, i.e., the detector device 23, one can simulate various structures, for example by introducing cork and other materials. This allows do create an image of a realistic model for a 3-D dosimetry of the simulated tumor.

Thus, for example, the data from an alternative detection of the tumor movement can be combined with the result of the data that have been obtained by means of the simulated measurements in the 3D dosimetry in order to calculate a perspective tumor movement. Thus it is for example possible to supply the calculated expected tumor movement to a control algorithm, so that during the irradiation of the patient by means of the radiotherapy device, an improved, if not quite optimized, movement compensation of the tumor movement is achieved. The control device 3 could then calculate, online and in advance, a "displacement vector" of the tumor position and compare with the online data from the "alternative detection". In this manner, the movement of the tumor could be at least partially compensated for by an opposite movement of the robot arm 2.

FIG. 5 shows a further radiotherapy device. Unless stated otherwise, the components of the radiotherapy device shown in FIG. 5, which are essentially structurally and functionally identical with the components of the radiotherapy device shown in FIG. 1, are provided with the same reference numerals.

The radiotherapy device shown in FIG. 5 mainly differs from the radiotherapy device illustrated in FIG. 1 in that the treatment table 1 is not held by the robot arm 2, but by means of a lifting device 52.

To check the radiotherapy device shown in FIG. 5, a further measuring device 51 can be used for dosimetry in radiotherapy. In the case of the present embodiment, it comprises the water phantom 21 and a hexapod 53 as an automatic mechanical device for moving the water phantom 21.

In addition to the mechanical part 54 of the hexapod 53, with which the water phantom 21 can be moved, the hexapod 53 comprises a control device 55 which is designed to move the mechanical part 54 of the hexapod 53 so that a movement of the patient during the irradiation is simulated. The movement of the patient during the irradiation is caused, for example by respiration of the patient. To suitably move the mechanical part 54 of the hexapod 53, a suitable computer program is running in particular in the control device 55, so that the control device 55 actuates the mechanical component 54 of the hexapod 53 in such a manner that the water phantom 21 performs the simulated movement. To simulate the movement of the patient, for example, a mathematical motion model of the patient is stored in the control device 55.

During the simulation, the hexapod 53 with the water phantom 21 is placed on the treatment table 1 and is irradiated by means of the radiotherapy radiation source 4.

What is claimed is:

1. A measuring device for dose measurement in radiation therapy, comprising:
    a water phantom having a detector device that is designed to detect ionizing radiation, the detector device configured to obtain a three-dimensional radiation dose distribution based on radiation of the phantom;
    a mechanical device, which is designed to move the water phantom; and
    a control device, which is designed to control the mechanical device in such a manner that it moves the water phantom to simulate respiration movement of a patient during irradiation with a radiotherapy device;
    wherein the mechanical device is a robot arm having a plurality of successive links connected by joints, the links being movable relative to each other in relation to their axes.

2. The measuring device according to claim 1, wherein the water phantom comprises a container filled with a liquid, in which the detector device is arranged.

3. The measuring device according to claim 1, wherein the detector device comprises a main body and at least one detector means that is arranged or can be arranged in and/or on the main body.

4. The measuring device according to claim 3, wherein the main body has an inner main body and an outer main body, which encloses the inner main body.

5. The measuring device according to claim 3, wherein the at least one detector means comprises at least one X-ray film.

6. The measuring device according to claim 3, wherein said at least one detection means comprises at least one radiation detector arranged in and/or on the main body.

7. The measuring device of claim 5, wherein the main body comprises at least one slot adapted for receiving the at least one X-ray film.

8. The measuring device according to claim 1, wherein the control device controls the mechanical device to move the water phantom during irradiation with a radiotherapy device that comprises a therapeutic radiation source.

9. The measuring device of claim 1, wherein the control device combines data obtained from the phantom with measured patient sensor data to calculate potential tumor movement and predict the location of a tumor during treatment.

10. The measuring device of claim 1, wherein:
the detector device is configured to generate signals related to the detected radiation; and
the control device automatically evaluates the generated signals.

11. A method for checking a radiotherapy device comprising:
placing a water phantom on a treatment table of a radiotherapy device, which comprises a robot arm, a control device and a radiation source, wherein the robot arm has several links following in succession, which are connected by joints and are movable relative to one another with respect to their axes, the control device is designed to move the robot arm, and the water phantom comprises a detector device, which is configured to detect ionizing radiation,
irradiating water phantom placed on the treatment table by means of the radiation source and, controlled by the control device, simultaneously moving the robot arm so that the water phantom performs a movement simulating respiration movement of a patient, and
obtaining a three-dimensional radiation dose distribution with the detector device based on radiation of the phantom.

12. The method of claim 11, further comprising:
generating signals with the detector device related to the detected radiation; and
automatically evaluating the signals using the control device.

13. The method of claim 11, further comprising:
combining data obtained from the phantom with measured patient sensor data;
calculating potential tumor movement based on the combined data; and
predicting the location of a tumor during treatment using the calculated potential tumor movement.

14. A method according to claim 11, further comprising the following steps:
evaluating the detector device of the water phantom after irradiation, and
moving the treatment table with a robot during irradiation of the patient based on the evaluated detector device.

15. The method according to claim 11, wherein the radiotherapy device comprises a therapeutic radiation source.

* * * * *